US008064985B2

(12) United States Patent
Peterson

(10) Patent No.: US 8,064,985 B2
(45) Date of Patent: Nov. 22, 2011

(54) SYSTEM AND METHOD FOR DETERMINING THE POSITION OF A FLEXIBLE INSTRUMENT USED IN A TRACKING SYSTEM

(75) Inventor: Thomas Herbert Peterson, Wilmington, MA (US)

(73) Assignee: GE Medical Systems Global Technology Company, Waukesha, WI (US)

( * ) Notice: Subject to any disclaimer, the term of this patent is extended or adjusted under 35 U.S.C. 154(b) by 1890 days.

(21) Appl. No.: 10/660,825

(22) Filed: Sep. 12, 2003

(65) Prior Publication Data
US 2005/0059883 A1 Mar. 17, 2005

(51) Int. Cl.
*A61B 19/00* (2006.01)
(52) U.S. Cl. ......... 600/424; 606/130
(58) Field of Classification Search ......... 600/424; 73/862.451
See application file for complete search history.

(56) References Cited

U.S. PATENT DOCUMENTS

| | | | | |
|---|---|---|---|---|
| 4,722,348 A * | 2/1988 | Ligtenberg et al. | ......... | 600/488 |
| 5,058,570 A * | 10/1991 | Idemoto et al. | ......... | 601/4 |
| 5,339,799 A * | 8/1994 | Kami et al. | ......... | 600/117 |
| 5,722,419 A * | 3/1998 | Semmlow et al. | ......... | 600/546 |
| 5,803,089 A | 9/1998 | Ferre et al. | | |
| 6,109,270 A | 8/2000 | Mah et al. | | |
| 2003/0004439 A1 | 1/2003 | Pant et al. | | |
| 2007/0055142 A1* | 3/2007 | Webler | ......... | 600/425 |

FOREIGN PATENT DOCUMENTS

| | | |
|---|---|---|
| JP | 63241409 | 10/1988 |
| JP | 2002095630 | 4/2002 |
| WO | WO 02/36018 | 5/2002 |

OTHER PUBLICATIONS

Davidson, Tish. "Pulmonary artery catheterization". Encyclopedia of Medicine 20010406. FindArticles.com Dec. 12, 2007. http://findarticles.com/p/articles/mi_g2601/is_0011/ai_2601001143.*
Tanaka et al. Needle Deflection and Sewability on Lockstitch Sewing Machine. Journal of the Textile Machinery Society of Japan. vol. 43(3) p. 71-78. 1997.*

* cited by examiner

*Primary Examiner* — Brian Casler
*Assistant Examiner* — Parikha S Mehta
(74) *Attorney, Agent, or Firm* — McAndrews, Held & Malloy, Ltd.; William Baxter

(57) ABSTRACT

A medical instrument for use in an image guided surgery system, including a support member operatively connected to a flexible engaging member, and a strain gauge affixed to a portion of the flexible engaging member. The strain gauge is configured to detect deflection of the flexible engaging member.

23 Claims, 5 Drawing Sheets

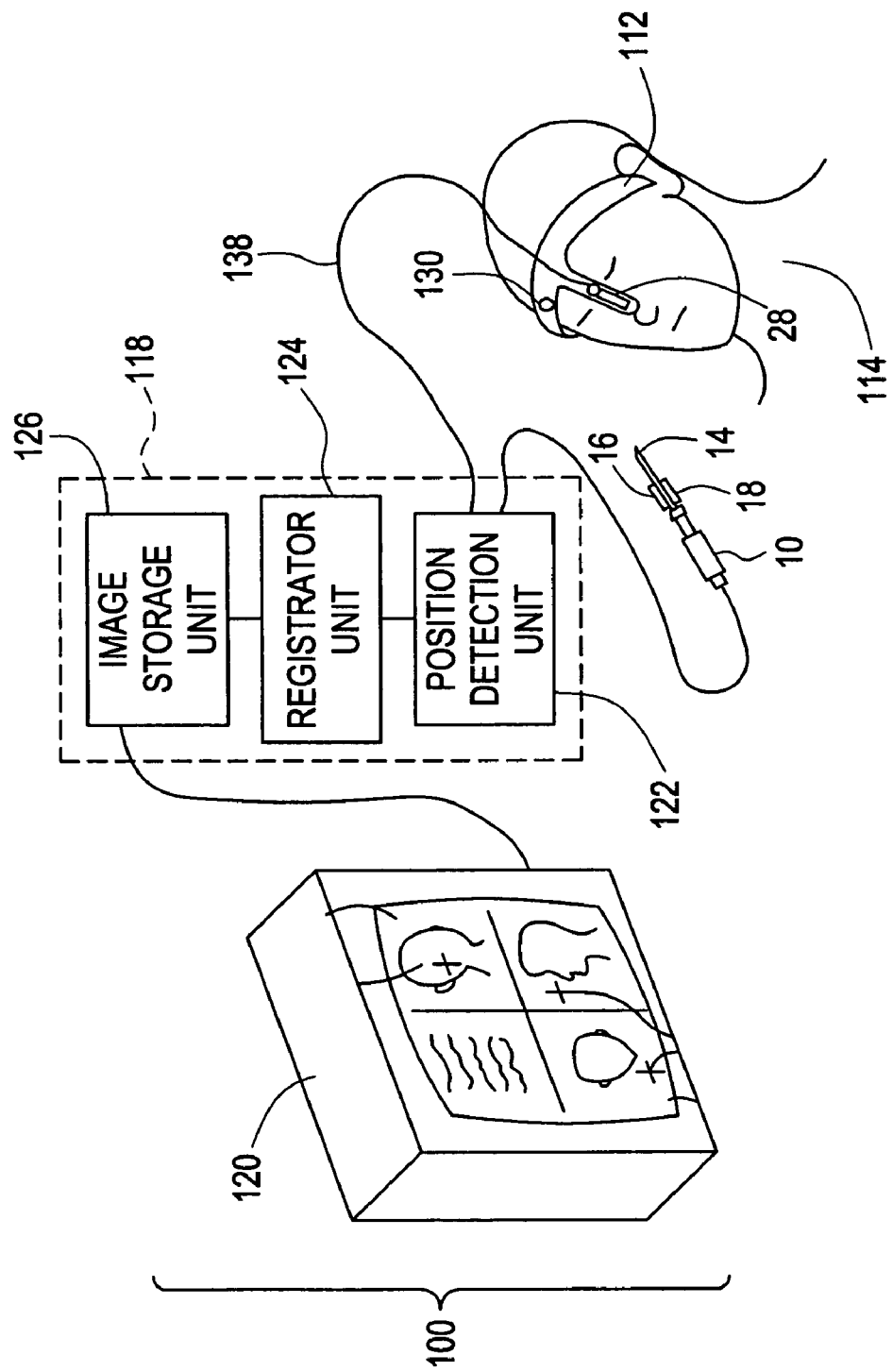

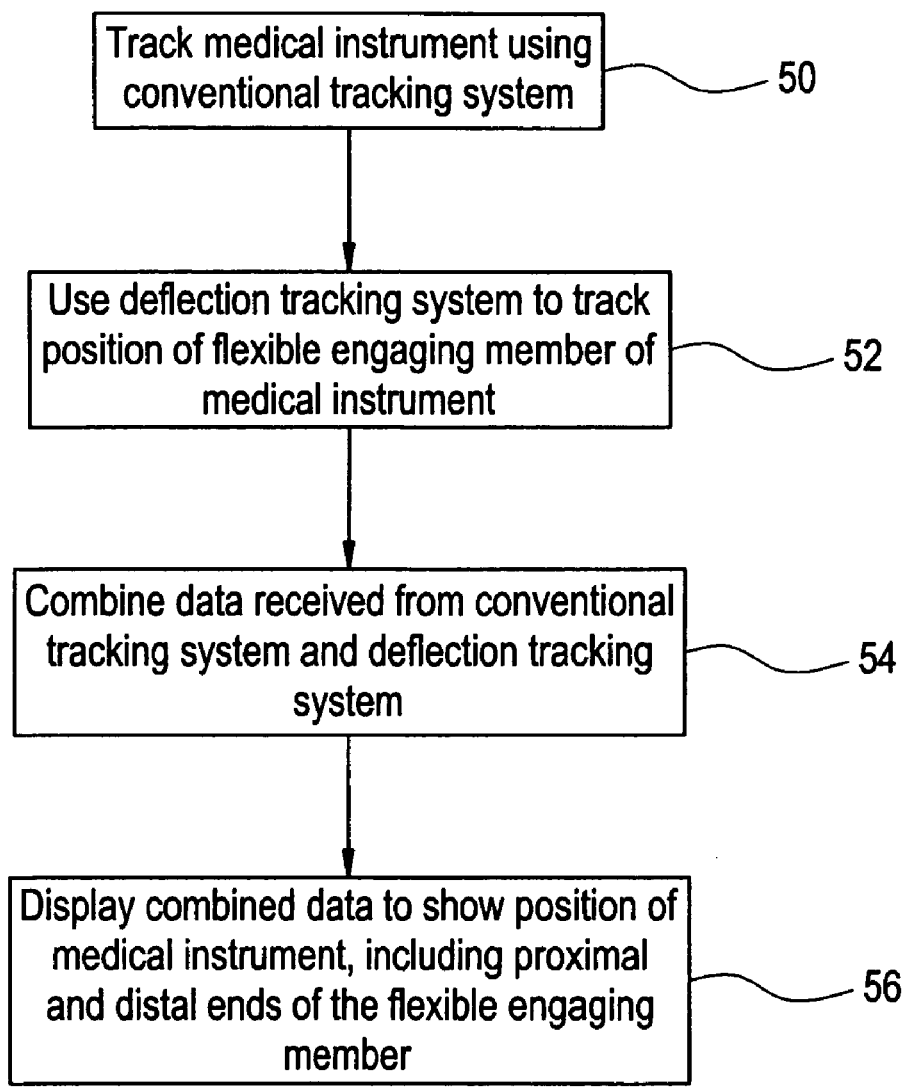

SYSTEM AND METHOD FOR DETERMINING THE POSITION OF A FLEXIBLE INSTRUMENT USED IN A TRACKING SYSTEM

BACKGROUND OF THE INVENTION

The present invention generally relates to flexible instruments, such as needles, probes, catheters, curettes and the like, used in image guided applications, such as image guided surgery. In particular, the present invention relates to a system and method for determining the position of a flexible instrument during an image guided application.

Many medical procedures involve a medical instrument, such as a drill, a catheter, scalpel, scope, stent or other tool. In some cases, a medical imaging or video system may be used to provide positioning information for the instrument, as well as visualization of an interior of a patient. However, medical practitioners often do not have the use of medical imaging systems when performing medical procedures. Typically, medical imaging systems are too slow to produce useable real-time images for instrument tracking in medical procedures. The use of medical imaging systems for instrument tracking may also be limited for health and safety reasons (e.g., radiation dosage concerns), financial limitations, physical space restrictions, and other concerns, for example.

Medical practitioners, such as doctors, surgeons, and other medical professionals, often rely upon technology when performing a medical procedure, such as image-guided surgery or examination. A tracking system may provide positioning information of the medical instrument with respect to the patient or a reference coordinate system, for example. A medical practitioner may refer to the tracking system to ascertain the position of the medical instrument when the instrument is not within the practitioner's line of sight. A tracking system may also aid in presurgical planning.

The tracking or navigation system allows the medical practitioner to visualize the patient's anatomy and track the position and orientation of the instrument. The medical practitioner may use the tracking system to determine when the instrument is positioned in a desired location. The medical practitioner may locate and operate on a desired or injured area while avoiding other structures. Increased precision in locating medical instruments within a patient may provide for a less invasive medical procedure by facilitating improved control over smaller instruments having less impact on the patient. Improved control and precision with smaller, more refined instruments may also reduce risks associated with more invasive procedures such as open surgery.

Tracking systems may be ultrasound, inertial position, optical or electromagnetic tracking systems, for example. U.S. Pat. No. 5,803,089, entitled "Position Tracking and Imaging System for Use in Medical Applications," issued to Ferre, et al. (the "'089 patent"), and U.S. Pat. No. 6,484,049, entitled "Fluoroscopic Tracking and Visualization System," issued to Seeley, et al. (the "'049 patent") both describe surgical tracking and navigation systems. The '089 patent and the '049 patent are hereby incorporated by reference in their entireties. Tracking systems using optical detection (video camera and/or CCDs (Charge Coupled Devices)) have been proposed for monitoring the position of a medical instrument with respect to a reference unit as mentioned in U.S. Pat. No. 5,230,623, entitled "Operating Pointer with Interactive Computergraphics," issued to Guthrie, et al. (the "'623 patent"). Further, tracking systems using ultrasonic detection are also disclosed in the '623 patent Electromagnetic tracking systems may employ coils as receivers and transmitters. Typically, an electromagnetic tracking system is configured in an industry-standard coil architecture (ISCA). ISCA uses three colocated orthogonal quasi-dipole transmitter coils and three colocated quasi-dipole receiver coils. Other systems may use three large, non-dipole, non-colocated transmitter coils with three colocated quasi-dipole receiver coils. Another tracking system architecture uses an array of six or more transmitter coils spread out in space and one or more quasi-dipole receiver coils. Alternatively, a single quasi-dipole transmitter coil may be used with an array of six or more receivers spread out in space.

The ISCA tracker architecture uses a three-axis dipole coil transmitter and a three-axis dipole coil receiver. Each three-axis transmitter or receiver is built so that the three coils exhibit the same effective area, are oriented orthogonally to one another, and are centered at the same point. If the coils are small enough compared to a distance between the transmitter and receiver, then the coil may exhibit dipole behavior. Magnetic fields generated by the trio of transmitter coils may be detected by the trio of receiver coils. Using three approximately concentrically positioned transmitter coils and three approximately concentrically positioned receiver coils, for example, nine parameter measurements may be obtained. From the nine parameter measurements and a known position or orientation parameter, a position and orientation calculation may determine position and orientation information for each of the transmitter coils with respect to the receiver coil trio with three degrees of freedom.

Typically, conventional tracking system such as those discussed above, are used to track rigid medical instruments, such as aspirating devices, surgical drills, cutting instruments and the like. However, various surgical applications use flexible instruments such as curettes, needles, catheters, endoscopes, wires and the like that may deflect while navigated within an operating space of a patient. The conventional tracking systems usually are not capable of tracking the deflecting tips of these flexible instruments. Rather, these systems typically accurately track only a proximal end of the instrument that does not deflect. Hence, the systems may display a position of the medical instrument that is not accurate. A surgeon or physician may move the instrument based on the inaccurate information and damage internal structures of the patient.

Thus, a need exists for a system and method that accurately tracks the position of a medical instrument, including a distal operative end of the medical instrument.

SUMMARY OF THE INVENTION

Certain embodiments of the present invention provide a medical instrument for use in an image guided surgery system. The medical instrument includes a support member operatively connected to a flexible engaging member, and a strain gauge affixed to a portion of the flexible engaging member. The strain gauge is configured to detect deflection of the flexible engaging member. The measured resistance of the strain gauge changes when the flexible engaging member deflects. The strain gauge is a resistor within an electrical circuit, such as a Wheatstone bridge, in which a potential difference occurs when the resistance of the strain gauge changes. The medical instrument may be used in an image guided surgery system that includes a tracking system that is separate and distinct from a deflection tracking system that includes the strain gauge(s). The additional tracking system may be an electromagnetic, optical, inertial position, or ultrasound tracking system configured to track the medical instrument.

The flexible engaging member may be a needle, catheter, curette, endoscope, or K wire. The medical instrument may include at least one additional strain gauge affixed to the flexible engaging member. The strain gauge(s) is affixed to a portion of the flexible engaging member that is proximate to the support member.

Certain embodiments of the present invention also provide a method of navigating a medical instrument having a flexible engaging member used in image guided surgery. The method includes tracking the medical instrument with a first position tracking method that tracks a proximal end of the medical instrument; and using a second tracking method to track deflections of an operative member of the medical instrument located at a distal end of the medical instrument. The method also includes combining data received and displaying a position of the medical instrument based on the combined data.

BRIEF DESCRIPTION OF SEVERAL VIEWS OF THE DRAWINGS

FIG. 6 illustrates an electromagnetic tracking system according to an embodiment of the present invention.

FIG. 7 illustrates a flow chart of a method of accurately tracking a position of a medical instrument during image guided surgery.

Figure 1:
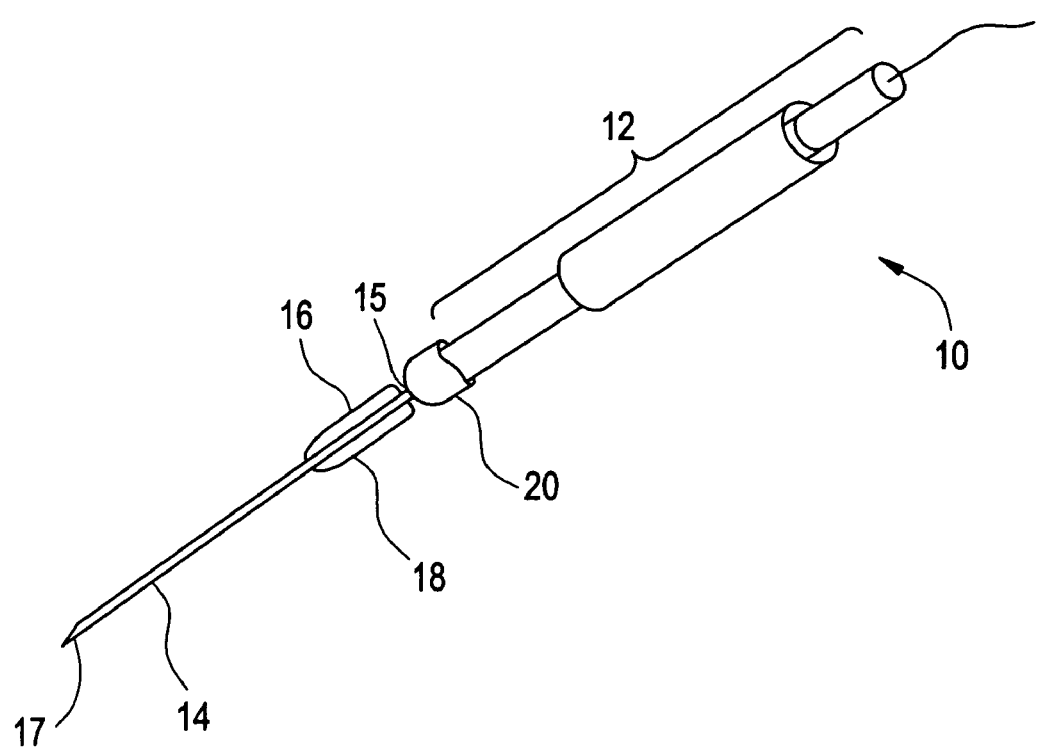
FIG. 1 illustrates a medical instrument according to an embodiment of the present invention.

The foregoing summary, as well as the following detailed description of certain embodiments of the present invention, will be better understood when read in conjunction with the appended drawings. For the purpose of illustrating the invention, there is shown in the drawings, certain embodiments. It should be understood, however, that the present invention is not limited to the arrangements and instrumentalities shown in the attached drawings.

DETAILED DESCRIPTION OF THE INVENTION

FIG. 1 illustrates a medical instrument 10 according to an embodiment of the present invention. The medical instrument 10 includes a rigid support member 12, such as a handle, a main body housing electronics and the like, or mounting assembly, and a flexible tip or engaging member 14. The flexible engaging member 14 includes a proximal end 15 (near the support member) and a distal operative end 17. The flexible engaging member 14 is the operative end of the medical instrument 10. The flexible engaging member may be a flexible probe, needle, curette, K wire, catheter or various other such devices that are susceptible to deflection, flexing, and other such movements.

Strain gauges 16 and 18 are positioned on the flexible engaging member 14 proximate a distal end 20 of the support member 12. The strain gauges 16 and 18 are configured to detect deflection in the flexible engaging member 14, as discussed below. The strain gauges 16 and 18 may be positioned on any portion of the flexible engaging member 14. However, the strain gauges 16 and 18 are preferably positioned on a portion of the flexible engaging member 14 that substantially bends, or deflects, when a force is applied to the flexible engaging member 14. For example, the strain gauges 16 and 18 may be positioned proximate the support member 12 of the medical instrument.

Figure 2:
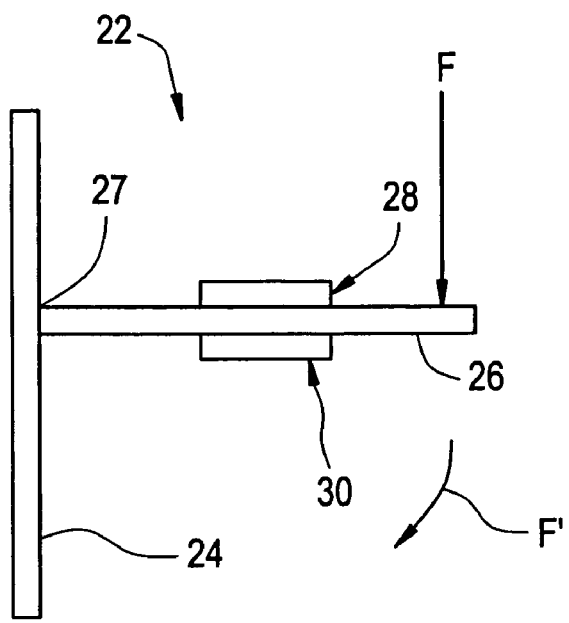
FIG. 2 illustrates a simplified diagram of a strain gauge according to an embodiment of the present invention.

FIG. 2 illustrates a simplified diagram of a strain gauge system 22 according to an embodiment of the present invention. The system 22 includes a rigid support 24, a flexible member 26 extending perpendicularly from the rigid support 24, and an upper strain gauge 28 and a lower strain gauge 30 affixed to the flexible member 26. The rigid support 24 is analogous to the distal end of the support member 12, while the flexible member 26 is analogous to the flexible engaging member 14 shown in FIG. 1.

Figure 3:
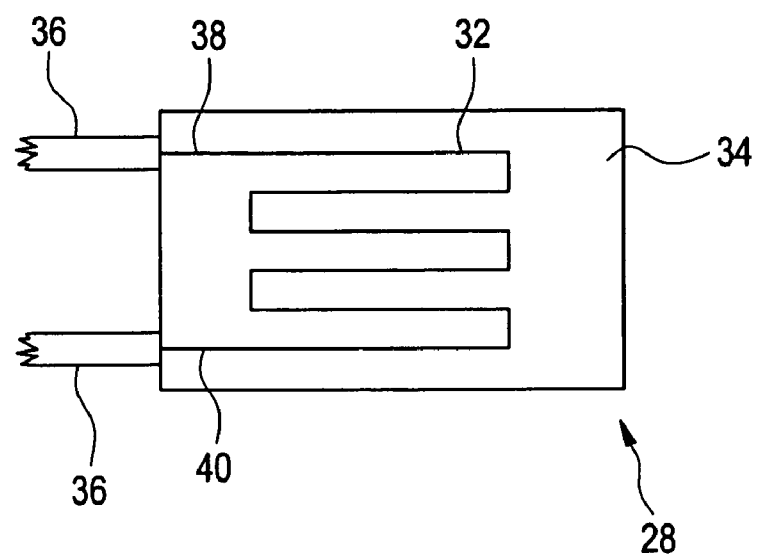
FIG. 3 illustrates a top view of a strain gauge according to an embodiment of the present invention.

FIG. 3 illustrates a top view of a strain gauge 28 or 30. Each strain gauge 28 and 30 includes a piece of wire 32 bonded to a flexible plastic backing 34. Connecting leads 36 electrically connect the ends 38, 40 of the wire to other elements within an electrical circuit (not shown).

Referring again to FIG. 2, when a force is applied to the flexible member 26 in the direction of F, thereby moving the flexible member 26 in an arcuate path about a pivot point 27 in the direction of F', the length of the upper strain gauge 28 increases and its cross-sectional area decreases. As the length of the upper strain gauge 28 increases and its cross-sectional decreases, the resistance of the upper strain gauge 28 increases, as shown by equation (1):

$$R = \rho L/A \tag{1}$$

where
R=resistance,
L=length of the strain gauge,
A=cross sectional area of the strain gauge, and
$\rho$=resistivity of the strain gauge.

Further, when the flexible member 26 is moved in the direction of F', the length of the lower strain gauge 30 decreases, and its cross-sectional area increases, thereby causing the resistance of the lower strain gauge 30 to decrease. The changes in resistance may be detected by a Wheatstone bridge circuit as shown in FIG. 4.

Figure 4:
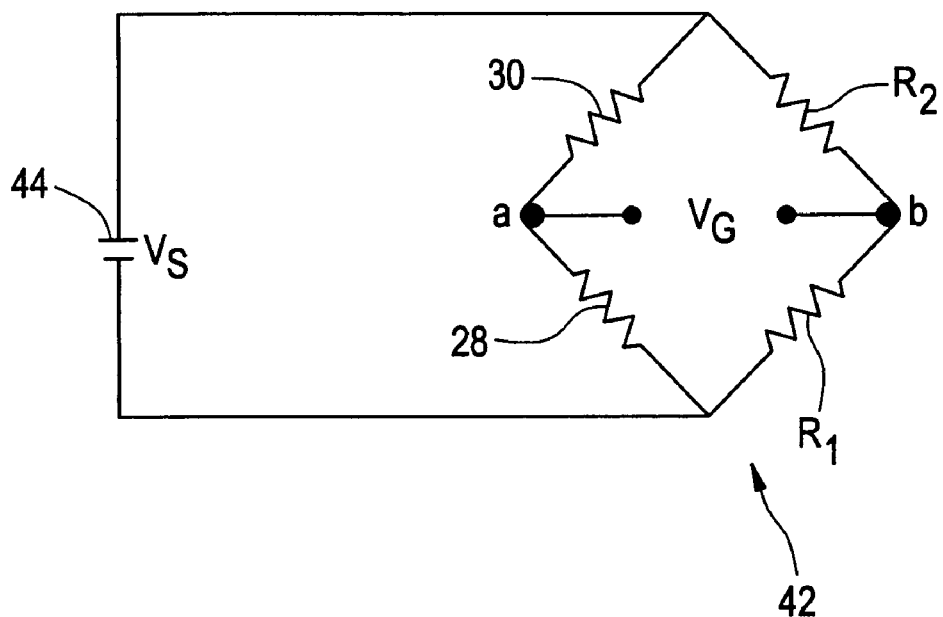
FIG. 4 is a circuit diagram of a Wheatstone bridge according to an embodiment of the present invention.

FIG. 4 is a circuit diagram of a Wheatstone bridge 42 according to an embodiment of the present invention. The Wheatstone bridge 42 includes resistors $R_1$ and $R_2$, strain gauges 28 and 30 (shown as resistors), and a source of electromotive force (emf) 44. The strain gauges 28 and 30 are used within the Wheatstone bridge 42. Resistors $R_1$ and $R_2$ are selected such that the Wheatstone bridge 42 is balanced when no force is applied to the flexible member 26 of the strain gauge system 22 shown in FIG. 2. When the Wheatstone bridge 42 is balanced, there is no potential difference between the points a and b. However, when a force is applied to the flexible member 26, the resistance of each strain gauge 28 and 30 changes and the Wheatstone bridge 42 is no longer balanced. Consequently, a potential difference appears between points a and b that is proportional to the magnitude of the force applied to the flexible member 26.

Referring again to FIG. 2, the strain gauge system 22 is configured to output a change in resistance that is directly proportional to the amount of force applied in the direction of F. For example, if a force of magnitude $F_1$ is applied to the flexible member 26, a potential difference appears between points a and b of the Wheatstone bridge. Further, the flexible member will move a particular distance over path F' as a result of the force $F_1$ applied. Thus, a potential difference $V_1$ is directly proportional to a distance of deflection over the path F'. A direct linear relationship exists between the amount of deflection and the potential difference. The distance the flexible member deflects yields a unique potential difference $V_{EX}$. Consequently, various potential differences output from a circuit having the strain gauges 28 and 30 allow one to know the amount the flexible member 26 deflects. Equation (2) shows the relationship between strain/compression and potential difference:

$$V_S/V_G = (G(e))/2 \quad (2)$$

where $V_S$=voltage supplied, $V_G$32 potential difference due to strain/compression, G=a gauge factor, and e=the amount of strain/compression.

The strain/compression of a strain gauge, such as strain gauges 28 and 30, yields a potential difference $V_G$. The potential difference may be correlated to the strain/compression. That is, a measurement of potential difference allows one to determine the amount of strain/compression of the strain gauges 28 and 30. Further, an amount of strain/compression allows one to know the amount the flexible member 26 deflects. Each measured potential difference allows one to determine the amount of strain/compression on the strain gauge 28 or 30, which in turn provides information regarding the amount of deflection of the flexible member 26. Thus, each particular potential difference may be correlated to an amount of deflection of the flexible member 26. A measurement of the potential difference $V_G$ allows one to calculate an amount of deflection of the flexible member 26.

Turning again to FIG. 1, the principles described above may be applied to the medical instrument 10. The strain gauges 16 and 18 are affixed above and below the flexible engaging member 14. Thus, as the flexible engaging member 14 is deflected, the strain gauges 16 and 18 strain or compress. As the strain gauges 16 and 18 strain or compress, the lengths and cross-sectional areas of the strain gauges change, as described above. For example, as a strain gauge 16 or 18 strains, its length increases and its cross-sectional area decreases, thereby increasing its resistance. Further, if a strain gauge 16 or 18 compresses, its length decreases and its cross-sectional area increases, thereby decreasing its resistance. Because the strain gauges are included within a Wheatstone bridge circuit 42, as shown in FIG. 4, a potential difference arises within the Wheatstone bridge circuit that is proportional to the distance of deflection of the flexible engaging member 14. Each measured potential difference corresponds directly to an amount of deflection of the flexible engaging member 14.

Figure 5:
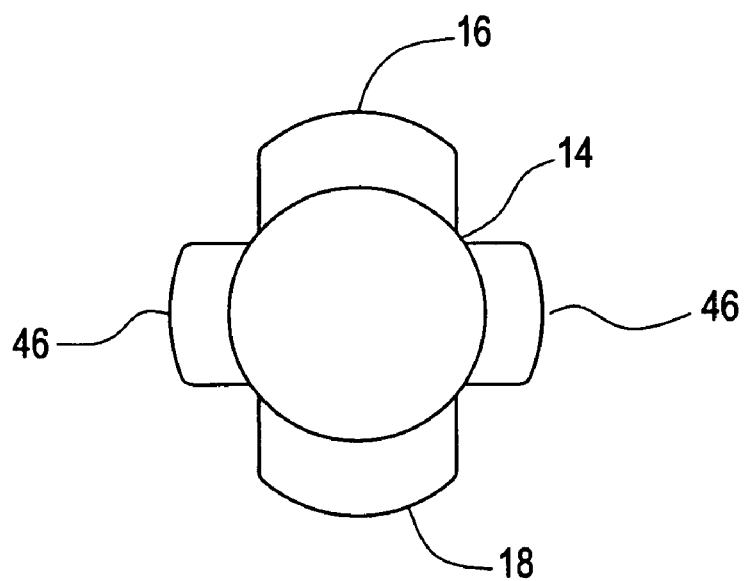
FIG. 5 illustrates a cross-sectional axial view of a flexible engaging member according to an alternative embodiment of the present invention.

FIG. 5 illustrates a cross-sectional axial view of the flexible engaging member 14 according to an embodiment of the present invention. The flexible engaging member 14 includes the upper strain gauge 16 and the lower strain gauge 18. The flexible member 14 may also have lateral strain gauges 46 affixed thereto for providing additional information regarding lateral deflection of the flexible engaging member 14. Optionally, the strain gauges 16, 18, and 46 may be solid state strain gauges.

FIG. 6 illustrates an electromagnetic tracking system 100 according to an embodiment of the present invention. The system 100 includes a headset 112 mounted on a patient 114, the medical instrument 10, a control system 118, and a display 120. The control system 118, which is in electrical communication with the medical instrument 10, the headset 112 and the display 120, includes a position detection unit 122, a registration unit 124, and an image storage unit 126. The image storage unit 126 stores sets of prerecorded images such as CAT, MRI, or PET scan images. Each set of images may be taken along, for example, coronal, sagittal or axial directions.

The system 100 also includes a receiver assembly, including magnetic sensors, positioned on the headset 112. The receiver assembly is configured to detect a magnetic field. A transmitter assembly is positioned on the medical instrument 116. The transmitter assembly is configured to generate a magnetic field that is detected by the receiver assembly. Alternatively, the receiver assembly may be positioned on the medical instrument 16, while the transmitter assembly may be positioned on the headset 12. Optionally, the medical instrument 10 may be used with various other tracking systems, such as ultrasound, inertial position and optical tracking systems.

The system 100 operates to track the medical instrument 10 with respect to the headset 12 through various methods known in the art. The control system 118 tracks the medical instrument through electromagnetic tracking and through the strain gauges 16 and 18. As the medical instrument 10 is inserted into the patient 14, the flexible engaging member 14 may deflect, as described above, as it encounters anatomical structures within the patient 14.

The general position of the medical instrument 10 may be tracked through electromagnetic tracking. That is, an electromagnetic tracking system may accurately track the proximal end 15, i.e., the end closest to the support member 12, of the flexible engaging member 14. The deflection of the distal end 17 of the flexible engaging member 14 is detected by a deflection tracking system that includes the strain gauges 16 and 18. The strain gauges 16 and 18, which are in electrical communication with the control system 118, relay deflection data signals to the control system 118. The control system 118 then processes both the information received from the electromagnetic tracking members (i.e., the receiver assembly and the transmitter assembly) and the strain gauges 16 and 18. The control system 118 correlates received data from the strain gauges with amounts of deflection of the flexible engaging member 14. The control system 118 then combines the electromagnetic tracking information with the deflection data and displays a position of the medical instrument 10, including the position of the flexible engaging member 14, on the display 120 over previously obtained images of the patient.

FIG. 7 illustrates a flow chart of a method of accurately tracking a position of the medical instrument 10 during image guided surgery. At 50, the medical instrument 10 is tracked using conventional image guided surgery tracking methods. For example, the medical instrument 10 may be tracked through an electromagnetic, optical, or inertial position tracking system. The conventional tracking system accurately tracks a general position of the medical instrument 10. The conventional tracking system accurately tracks the support member 12 and the proximal end 15 of the medical instrument 14.

At the same time that the medical instrument 10 is tracked by the conventional tracking system, the medical instrument is tracked by the deflection tracking system, including strain gauges at 52. The deflection tracking system tracks the deflection of the flexible engaging member 14 of the medical instrument as described above.

At 54, a control system, such as a microprocessor, processes and combines data received from the conventional tracking system and the deflection tracking system. Then, at 56, the processor displays the combined data on a monitor to show the position of the medical instrument 10, including the proximal and distal ends 15, 17 of the flexible engaging member 14.

Embodiments of the present invention provide a system and method in which a medical instrument may be tracked by a conventional tracking system using methods known in the art. The tracking system provides information regarding the general position of the medical instrument. The use of the strain gauges on the medical instrument provides a deflection tracking system that provides more specific information regarding the location of the tip (i.e., the flexible engaging member 14) of the medical instrument 10. Using information provided by a conventional tracking system and information provided by the deflection tracking system provides accurate information regarding the location of the medical instrument.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A medical instrument for use in an image guided surgery system, comprising:
   a medical instrument comprising:
   a support member operatively connected to a flexible engaging member having an operative distal tip;
   upper and lower strain gauges affixed to an outer portion of said flexible engaging member, wherein said upper and lower strain gauges are configured to detect movement of said operative distal tip of said flexible engaging member and generate deflection data signals;
   a tracking system configured to track said medical instrument;
   a control system configured to correlate said deflection data signals from said upper and lower strain gauges with amounts of deflection of the flexible engaging member and further configured to combine tracking information from the tracking system with the deflection data; and
   a display configured to display a position of the medical instrument including the position of the flexible engaging member over previously obtained images of a patient.

2. The medical instrument of claim 1, wherein a resistance of said strain gauge changes when said flexible engaging member deflects.

3. The medical instrument of claim 2, wherein said strain gauge is within an electrical circuit in which a potential difference occurs when said resistance of said strain gauge changes.

4. The medical instrument of claim 1, wherein said flexible engaging member is one of a needle, catheter, curette, and K wire.

5. The medical instrument of claim 1, further comprising at least one additional strain gauge affixed to said flexible engaging member.

6. The medical instrument of claim 1, wherein said portion of said flexible engaging member is proximate to said support member.

7. The medical instrument of claim 1, wherein said strain gauge provides information regarding a location of said operative distal tip in relation to a longitudinal axis of said support member.

8. An image guided surgery system, comprising:
   a medical instrument having a flexible engaging member operatively connected to a support member, said flexible engaging member having a deflectable operative distal tip
   at least one of an electromagnetic, optical, inertial position, and ultrasound tracking system configured to track said medical instrument; and
   a deflection tracking system configured to track said flexible engaging member of said medical instrument, said deflection tracking system comprising at least one strain gauge affixed to an outer portion of said flexible engaging member in order to detect movement of said deflectable operative distal tip.

9. The image guided surgery system of claim 8, wherein a resistance of said at least one strain gauge changes when said flexible engaging member moves.

10. The image guided surgery system of claim 9, wherein said at least one strain gauge is within an electrical circuit in which a potential difference occurs when said resistance of said strain gauge changes.

11. The image guided surgery system of claim 10, further comprising a processing unit that correlates said potential difference with an amount of movement of said flexible engaging member.

12. The image guided surgery system of claim 8, further comprising a display for showing a position of said medical instrument within an operating area of a patient.

13. The image guided surgery system of claim 8, wherein said flexible engaging member is one of a needle, catheter, curette, and K wire.

14. The medical instrument of claim 8, wherein said portion of said flexible engaging member is proximate to said support member.

15. The image guide surgery system of claim 8, wherein said at least one strain gauge provides information regarding a location of said deflectable operative distal tip.

16. A method of navigating a medical instrument having a flexible engaging member having an operative distal tip, the method comprising:
   tracking the medical instrument with a first position tracking method that tracks a proximal end of the medical instrument; and
   using a second tracking method to track movement of the operative distal tip of the medical instrument, wherein said using comprises affixing a strain gauge on an outer portion of the operative distal tip of the medical instrument in order to detect movement of the operative distal tip.

17. The method of claim 16, comprising measuring a change in voltage that arises from a change in resistance of the strain gauge upon deflection of the operative distal tip.

18. The method of claim 17, wherein said affixing comprises affixing the strain gauge on the portion of the flexible engaging member that is proximate a support member of the medical instrument.

19. The method of claim 17, wherein said affixing comprises affixing at least one other strain gauge on the outer portion of the flexible member of the medical instrument.

20. The method of claim 17, further comprising correlating the change in voltage to an amount of deflection of the flexible engaging member.

21. The method of claim 16, further comprising combining data received from said tracking and using and displaying a position of the medical instrument based on the combined data.

22. The method of claim 16, wherein said first tracking method comprises one of an electromagnetic, optical, inertial position and ultrasound tracking method.

23. The method of claim 16, wherein said affixing the strain gauge on the outer portion of the operative distal tip of the medical instrument in order to detect movement of the operative distal tip provides information regarding a location of the operative distal tip.

\* \* \* \* \*